United States Patent [19]

Babcock et al.

[11] Patent Number: 5,252,319

[45] Date of Patent: Oct. 12, 1993

[54] AMINOSTEROIDS FOR OPHTHALMIC USE

[75] Inventors: John C. Babcock, Olga, Wash.; Jon R. Polansky, Mill Valley, Calif.; Lyle M. Bowman, Pleasanton, Calif.; Sheng-Wan Tsao, San Carlos, Calif.; Erwin C.-C. Si, Almeda, Calif.; Santosh K. Chandrasekaran, Moraga, Calif.

[73] Assignee: Insite Vision Incorporated, Alameda, Calif.

[21] Appl. No.: 836,866

[22] Filed: Feb. 19, 1992

Related U.S. Application Data

[62] Division of Ser. No. 537,062, Jun. 12, 1990, Pat. No. 5,124,154.

[51] Int. Cl.$^5$ .................. A61K 47/28; A61K 31/58; A61K 37/22

[52] U.S. Cl. .................. 424/78.04; 424/427; 424/428; 424/450; 424/451; 424/464; 514/169; 514/170; 514/172; 514/176; 514/177; 514/178; 514/179; 514/180; 514/182; 514/774; 514/777; 514/781; 514/784; 514/785; 514/801; 514/912; 514/913; 514/914; 514/944

[58] Field of Search .............. 424/427, 428, 450, 451, 424/78.04, 464; 514/177, 178, 179, 180, 182, 912, 913, 914, 169, 170, 172, 176, 774, 777, 781, 784, 785, 801, 944

[56] References Cited

U.S. PATENT DOCUMENTS 5,099,019  3/1992  McCall et al. .................. 544/123
5,120,843  6/1992  McCall et al. .................. 544/295

FOREIGN PATENT DOCUMENTS 137542  9/1967  New Zealand .
153024  12/1970  New Zealand .
152836  4/1971  New Zealand .
159657  3/1972  New Zealand .
186631  5/1980  New Zealand .
190007  9/1980  New Zealand .
200475  8/1985  New Zealand .
215587  4/1986  New Zealand .
224288  12/1989  New Zealand .
222103  8/1990  New Zealand .
226433  6/1991  New Zealand .
231086  7/1991  New Zealand .
229649  12/1991  New Zealand .
0997682  2/1983  U.S.S.R. .

OTHER PUBLICATIONS

"U78517F, A Second Generation Lazaroid With Potent Anti-Oxidant and Cerebroprotective Activity in Models of CNS Injury and Ischemia," E. D. Hall et al, *Journal of Neurotrauma*, vol. 6, No. 3, Fall 1989, pp. 213-214.

"Inhibition of Carbon Tetrachloride-Induced Lipid Peroxidation in Rat Hepatic Microsomes-Dissociation from Hepatoprotective Effects In Vivo" T. W. Petry et al, Abstracts of the 4th Intn'l Symposium on Biological Reactive Intermediates, Jan. 14-17, 1990, Hosted by the Center for Toxicology, The University of Arizona, Tucson, Ariz.

"Effects of the Antioxidants U74006F, U78517G and N,N'-Diphenyl-p-phenylenediamine on Carbon Tetrachloride-Induced Toxicity in Precision-Cut Rat Liver Slices," G. H. I. Wolfgang et al, Abstracts of the 4th Intn'l Symposium on Biological Reactive Intermediates, Jan. 14-17, 1990 Hosted by The Center for Toxicology, The University of Arizona, Tucson, Ariz.

"Modulation of Diquat-Induced Toxicity In Vitro by Novel Inhibitors of Lipid Peroxidation and the Antioxidant Diphenyl-p-phenylenediamine," R. A. Jolly et al, *The Toxicologist*, Abstracts of the 29th Annual Meeting, vol. 10, No. 1, Feb. 1990.

"Inhibition of Diquant-Induced Lipid Peroxidation and Toxicity In Vitro by Novel Antioxidants," G. H. I. Wolfgang et al, The Toxicologist, Abstracts of the 29th Annual Meeting, vol. 10, No. 1, Feb. 1990.

*Primary Examiner*—Thurman K. Page
*Assistant Examiner*—Carlos Azpuru
*Attorney, Agent, or Firm*—Howrey & Simon

[57] ABSTRACT

Methods and compositions for preventing or treating ophthalmic diseases or disorders wherein an ophthalmically effective amount of the $C_{20}$ through $C_{26}$ aminosteroids of formula XI and their pharmaceutical, acceptable salts, hydrates or solvates is administered in an inert vehicle to arrest oxidation processes damaging to the eye.

17 Claims, No Drawings

AMINOSTEROIDS FOR OPHTHALMIC USE

This application is a divisional of application Ser. No. 07/537,062, filed Jun. 12, 1990, now U.S. Pat. No. 5,124,154.

BACKGROUND OF THE INVENTION

The present invention relates to the prevention and treatment of eye diseases or disorders. More particularly, this invention relates to compositions and methods for arresting oxidation processes damaging to the eye.

It is known that oxygen-derived radical species are important mediators of several forms of tissue damage, such as ischemic and traumatic injuries to organs and tissues, inflammatory responses, and injuries which result from the intra-cellular metabolism of chemicals and drugs. In particular, oxygen-derived radical species have been suggested as destructive forces in such maladies as head and spinal cord injury, stroke, shock, Parkinsonism, muscular dystrophy, emphysema, ARDS (acute respiratory distress syndrome), asthma, aging, postmyocardial infarct tissue destruction, drug toxicity, radiation damage, transplant rejection, and burn damage.

The reduction of oxygen occurs in several stages which progressively include the super-oxide anion, hydrogen peroxide, hydroxyl radical, and finally water. Various biological processes can generate these species from oxygen or oxygen-derived materials. For example, phagocytosis, cytochrome P450 metabolic pathways, the biosynthesis of prostaglandins and leukotrienes, xanthine/xanthine oxidase, mitochondrial electron transport, and lipid peroxidation can all generate reactive oxygen species.

One target for damage by oxygen-derived radical species is the cell membrane. Oxidative damage at the cell membrane is enhanced by lipid peroxidation which is a chain reaction that alters or destroys the polyunsaturated fatty acids of the membrane phospholipids. Membrane bound proteins are also affected. The structural integrity and the function of cell membranes are irreversibly changed. Extra-cellular calcium can enter the cell, and calcium-dependent phospholipases and protein kinases are activated. These phospholipases, once activated, will cleave fatty acids from phospholipids and cause additional change in the chemical composition and physiologic state of the cell membrane. The free fatty acids are converted by cyclooxygenases to prostaglandins and thromboxanes. Inflammatory agents like a variety of HETES are also generated by lipoxygenases. In addition, new radical species are formed during the cascade. Radical attack by hydrogen peroxide of unsaturated fatty acids may be catalyzed by iron near or within the cell membrane. Iron can convert lipid hydroperoxides to peroxy and alkoxy radicals. It can interact with molecular oxygen or reduced oxygen radical species.

Lipid peroxidation normally proceeds as a radical driven chain reaction involving oxygen where the lipid peroxyl radical (LOO.) formed through initiation (reactions 1 and 2) attacks a second unsaturated fatty acid (reaction 3).

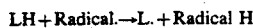

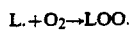

$\alpha$-Tocopherol (Vitamin E) inhibits lipid peroxidation by scavenging LOO. (reaction 4), preventing lipid radical chain reactions from occurring, and is itself converted into a radical

The $\alpha$TC radical then decomposes to tocopherolquinone and other products and thus, effectively terminates the chain reaction.

In addition to their adverse effects on various body tissues (e.g., as described above), oxidation reactions can also cause damage to the eye. It is known, for example, that the aqueous humor of the eye is rich in hydrogen peroxide and that the anterior tissues bathed by the aqueous humor exist in an extraordinarily oxidative environment. It is further known that prolonged exposure of the eye to light of certain wavelengths can cause harm to anterior, posterior and other tissues of the eye. Indeed, prolonged exposure to light produces oxidative damage in many tissues such as the lens, retina and retinal pigmented epithelium. Additionally, chronic exposure to light and to an oxidative environment is believed to induce cumulative damage, which, depending on the severity of the exposure and the susceptibilities of the individual exposed can result, in the best of cases in normal aging and discomfort and, in the worst of cases, in pathological disorders.

In addition to light exposure, such a cascade leading to the production of harmful oxidative species is initiated by inflammation, during trauma, following ischemia, during hemorrhaging, upon stimulation by a variety of drugs and endogenous cell regulators, upon pressure exertion on tissues as occurs diurnally as a result of introcular pressure changes in the anterior chamber of the eye, and indeed to a host of processes both normal and abnormal that occur continuously in the eye. Polyunsaturated fatty acids are also readily subjected to less specific chemical (non-enzymatic) oxidation to yield hydroperoxides, hydroxy fatty acids and malondialdehyde, materials which can contribute to the overall damage that accumulates with time.

Thus, oxidative processes are now known to play a role in age-related cataracts, light-induced retinal damage, other retinopathies such as diabetic retinopathy and age-related macular degeneration, inflammatory damage (such as that seen in uveitis), vascular leakage and edema (as in cystoid macular edema), accidental or surgical trauma, angiogenesis, corneal opacities, retolental fibroplasia, and some aspects of glaucoma.

To counteract the harmful effects of the oxidative processes described above, such as free radical-mediated lipid peroxidation, the body naturally produces a number of defensive compounds such as $\alpha$-tocopherol (vitamin E, which is an antioxidant), ascorbic acid, glutathione, catalase and superoxide dismutase. Thus, as set forth above, vitamin E is known to be a scavenger of both lipid peroxyl radicals and oxygen radicals, as well as to have a membrane-stabilizing action. Indeed, it is believed that chronic dietary vitamin E supplementation can attenuate postischemic cerebral hypoperusion by inhibiting the lipid peroxidative process.

A group of 21-aminosteroids have also been found to act as antioxidants, and some aminosteroids have been employed intravenously, intraperitoneally and orally in the treatment of central nervous system injury, head and spinal injury, and edema associated with acute stroke. It has been reported that intravenous administration of a citrate buffered saline solution of 0.15% by weight of U-74600F for treatment of spinal cord or brain injury has been effective to arrest lipid peroxideation therein. It is also known that in performing toxicology studies with various drugs, polysorbate 80 and hydroxypropylcellulose and the like can be used as suspending agents in low viscosity formulations.

International Publication Number WO 87/01706, which discloses a number of aminosteroids and their therapeutic use in a variety of contexts, as well as administration techniques and dosages, does not disclose treatment or prevention of ophthalmic diseases or disorders. Nor does it disclose topical application to the eye or administration by intraocular injection. Moreover, prior art formulations which cannot be comfortably and effectively applied to the eye have limited applicability.

In order to enhance the eye's ability to protect from damaging oxidative processes such as can occur with aging or due to a sudden trauma, it has been proposed to supply vitamin E to the eye by oral administration in view of its known ability to inhibit such oxidative processes. Vitamin E does scavenge free radicals and function as an antioxidant. However, it must be given chronically to have any effect. Moreover, even when administered chronically with other antioxidants, such as glutathione and vitamin C, the results are at best mixed.

SUMMARY AND OBJECTS OF THE INVENTION

It is a primary objective of the present invention to provide novel methods and compositions for improving visual function or for preventing loss of visual function in the eye of a human or other animal which is subject to oxidative intraocular damage and in need of such improvement or prevention.

More particularly, it is an object of the present invention to provide such methods and compositions which enhance the ability of the tissues of the eye to respond to trauma, to aging, to surgery, to the threat of glaucoma by increasing intraocular pressure, to the potential loss of vision from progression of macular degeneration and the like by supplementing, both acutely and chronically, the natural ability of the eye to resist oxidative damage.

It is a further object of the present invention to provide novel methods and compositions which help to preserve the natural antioxidants, such as vitamin E and superoxide dismutase, to exert their normal function of protecting the eye from oxidative insult as needed.

Yet another object of the present invention is to provide novel compositions and methods capable of preventing or ameliorating eye disease or injury, particularly by arresting oxidation processes damaging to the eye.

Still other objects of the present invention are to provide novel methods and novel compositions which employ amino-substituted steroid antioxidant agents.

It is still a further object of the present invention to provide such novel methods and compositions which can be given chronically or acutely.

In one aspect, the present invention involves methods of arresting processes (particularly oxidation processes) causing damage to the eye of a human or other animal that is subject to intraocular damage (particularly oxidative intraocular damage) and in need of improved visual function or prevention of its loss from such damage, wherein certain amino-substituted steroids which function as a therapeutic agent (particularly an antioxidant agent) are administered in an inert vehicle, to eye tissue by intraocular injection or topically. The term "inert vehicle" is broadly used herein to optionally include adjuvants, preservatives, buffers, demulcents and anything else that is essentially inert relative to the therapeutic function (particularly the antioxidant function) of the aminosteroids as that function relates to eye tissue.

When the intraocular injection is subconjunctival, a formulation containing between 0.01 and 5%, preferably between 0.05 and 2%, by weight of the aminosteroid therapeutic agent is administered; and preferably it is administered in a polymeric carrier such as a dextran or polysorbate 80 vehicle, with the formulations containing additives such as disodium edetate, sodium sulfite, and/or sodium chloride, and sodium hydroxide or hydrogen chloride for pH adjustment. When the intraocular injection is intracameral or intravitreal, a formulation containing between 0.001 and 1%, preferably between 0.005 and 0.15% especially when in solution, by weight of the aminosteroid therapeutic agent is administered; and preferably it is administered in a vehicle containing phosphate buffered saline, citrate buffered saline, or chrondroitin sulfate, or in a polymeric vehicle such as sodium hyaluronate, or hyaluronic acid, purified polyacrylamide or polysorbate 80, with the formulation containing sodium hydroxide or hydrogen chloride for pH adjustment.

When the administration is topical, a topical formulation containing between 0.01 and 10%, preferably between 0.1 and 5%, by weight of the agent is administered; and preferably it is administered in an aquequs polymeric solution, aqueous suspension, ointment, or gel vehicle. Except for ointments, these vehicles may contain liposomes for creating a reservoir of dissolved agent for contact with the tear film.

In another aspect, the present invention involves methods of preventing or treating ophthalmic diseases or disorders in a human or other animal that is subject to intraocular damage (particularly oxidative intraocular damage) and in need of improved visual function or prevention of its loss from such damage, wherein an ophthalmically effective amount of certain amino-substituted steroids which function as a therapeutic agent (particularly an antioxidant agent) is administered, in an inert vehicle, to arrest processes (particularly oxidation processes) damaging to the eye. As used herein, "ophthalmically effective amount" is that amount which, in the composition administered and by the technique administered, provides an amount of therapeutic agent to the involved eye tissues sufficient to improve visual function or prevent its loss for a desired period of time.

As mentioned above, it has been reported that intravenous administration of a citrate buffered saline solution of 0.15% by weight of U-74006F for treatment of spinal cord or brain injury has been effective to arrest lipid peroxidation therein. In a variety of animal species, acute systemic administration of U-74006F has produced adequate concentrations of active drug in the brain and in the spinal fluid and tissues to produce a dramatic protective effect. It is believed that a similar concentration in eye tissue will arrest oxidation processes damaging to the eye. Furthermore, we have found that a 100 uls of 0.15% U74006F citrate buffered solution, intravitreally injected into an eye, has been effective in the treatment of retinal ischemia in a rabbit model. That is an indication that there would be effective treatment of retinal diseases caused by glaucoma, diabetic retinopathy, and sudden trauma to the eye.

When administered systemically by intramuscular injection, formulations containing between 0.01 and 10%, preferably between 0.5 and 5%, by weight of the aminosteroid therapeutic agent are employed, preferably in a polysorbate 80, methyl cellulose, or other polymeric demulcent vehicle. When administered orally in an aqueous solution, aqueous suspension, elixer or other liquid, formulations containing between 0.05 and 5%, preferably between 0.1 and 2%, by weight of the aminosteroid therapeutic agent are employed. When administered orally as a solid, tablets, caplets or capsules containing between 1 and 100 mg of the aminosteroid therapeutic agent are employed. When administered intraveneously, formulations containing between 0.05 and 5%, preferably between 0.1 and 1%, by weight, of the aminosteroid therapeutic agent are employed, preferably in a citrate buffer or borate buffer carrier or in a lipid emulsion, unilamellar liposome or multilamellar liposome formulation.

In a further aspect, the present invention involves a composition for preventing or treating ophthalmic diseases or disorders, comprising:

(a) a selected amino-substituted steroid therapeutic agent, and (b) an inert ophthalmic vehicle, suitable for an ophthalmically topical or intraocular application, selected from polymeric solutions, suspensions, ointments or gels.

The aqueous carriers may contain liposomes for creating a reservoir of dissolved agent for contact with the tear film. Gels for topical ophthalmic application are the most preferred carriers. The composition contains an ophthalmically effective amount of aminosteroid therapeutic agent (particularly an antioxident agent) to arrest processes damaging to the eye (particularly oxidation processes). Any amount of agent present in dissolved form for immediate activity is present in an amount insufficient for local tissue damage, and at least some agent is present in suspension for activity upon dissolution. The viscosity of the composition is at least 5,000 cps, preferably at least 10,000 cps.

In all aspects of the invention, the amino-substituted steroid therapeutic agent is selected from the $C_{20}$ through $C_{26}$ aminosteroids of the formula XI structure, especially those which exhibit antioxidant functions, and pharmaceutically acceptable salts, hydrates, or solvates thereof. The formula XI structure is described and depicted in International Publication Number WO 87/01706, which is hereby incorporated by reference. More preferred are the $C_{21}$ aminosteroids of formula XI, especially those which inhibit lipid peroxidation, and pharmaceutically acceptable salts or hydrates thereof. Most preferred are U-74500, U-75412 and especially U-74006 and their pharmaceutically acceptable salts, hydrates or solvates, particularly U-74500A (the hydrochloride salt of U-74500), U-75412A (the hydrochloride salt of U-75412), and U-74006F (the mesylate salt of U-74006).

Advantageously, the amino-substituted steroid therapeutic agents may be administered chronically or acutely, while preventing tissue damage and minimizing any acute injury and preventing the onset of the diseased state.

With the foregoing as well as other objects, advantages, features and aspects of the invention that will become hereinafter apparent, the nature of the invention may be more clearly understood by reference to the detailed description of the invention and to the appended claims.

DETAILED DESCRIPTION OF PREFERRED EMBODIMENTS

The present invention encompasses methods and compositions for preventing or treating an ophthalmic disease or disorder, wherein an ophthalmically effective amount of certain amino-substituted steroids which function as a therapeutic agent (particularly an anti-oxidant agent), and an inert ophthalmic vehicle, are administered. Prior to discussing examples of the invention, a brief discussion is provided concerning the amino-substituted steroids themselves.

A number of recently developed amino steroids are described in great detail in Internation Publication Number WO 87/01706. Although lacking classic steroidal activities, some have been demonstrated to be among the most potent inhibitors of iron-dependent lipid peroxidation presently known. Indeed, some have been shown to have one or more of a multiplicity of antioxidant related actions including a vitamin-E-like scavenging of lipid peroxyl radicals, a scavenging of oxygen radicals, an alpha-tocopherol-sparing effect, a membrane stabilizing action, or an iron-binding property. Initial studies have shown that they may show promise in the acute treatment of head and spinal cord trauma, treatment of focal and global cerebral ischemia.

In the present invention, the amino substituted steroids employed are the $C_{20}$ through $C_{26}$ aminosteroids of the following formula XI structure as set forth in WO 87/01706, especially those which exhibit antioxidant functions.

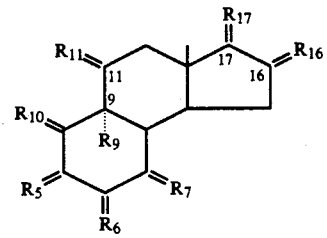

where:

(A-I) $R_6$ is $\alpha$-$R_{61}$:$\beta$-$R_{62}$, $R_{10}$ is $\alpha$-$R_{101}$:$\beta$-$R_{102}$ and $R_7$ is $\alpha$-H:$\beta$-H, where one of $R_{61}$ and $R_{62}$ is —H, and the other is —H, —F, or $C_1$-$C_3$ alkyl, $R_{102}$ is —$CH_3$, $R_{101}$ and $R_5$ taken together are —$(CH_2)_2$—C(—$R_{33}$)—CH= or —CH—CH—CO—CH=, where $R_{33}$ is =O or $\alpha$-H:$\beta$-$OR_{34}$ or $\alpha$-$OR_{34}$:$\beta$-H, where $R_{34}$ is —H, —P(=O) (OH)$_2$, —CO—$CH_3$, —CO—$C_2H_5$, —CO—$C_6H_5$, —CO—O—$CH_3$ or —CO—O—$C_2H_5$;

(A-II) $R_5$ is $\alpha$-$R_{53}$:$\beta$-$R_{54}$, $R_6$ is $\alpha$-$R_{63}$:$\beta$-$R_{64}$, $R_{10}$ is $\alpha$-$R_{103}$:$\beta$-$R_{104}$ and $R_7$ is $\alpha$-H:$\beta$-H, where one of $R_{63}$ and $R_{64}$ is —H, and the other taken together with one of $R_{53}$ and $R_{54}$ forms a second bond between $C_5$ and $C_6$, $R_{104}$ is —$CH_3$, $R_{103}$ and the other of $R_{53}$ and $R_{54}$ taken together are —$(CH_2)_2$—C(H)(OH)—$CH_2$— or —$(CH_2)_2$—C[H][OP(=O)—(OH)$_2$]—$CH_2$—;

(A-III) $R_{10}$ and $R_5$ taken together are =CH—CH=C(OR$_3$)—CH= where $R_3$ is —H, —p(=O)(OH)$_2$, $C_1$-$C_3$ alkyl, —CO— H, $C_2$-$C_4$ alkanoyl or benzyl, $R_6$ is $\alpha$-$R_{65}$:$\beta$-$R_{66}$ where one of $R_{65}$ and $R_{66}$ is —H, and the other is —H, —F, or $C_1$-$C_3$ alkyl and $R_7$ is $\alpha$-H:$\beta$-H;

(A-IV) $R_5$ is $\alpha$-$R_{57}$:$\beta$-$R_{58}$, $R_6$ is $\alpha$-$R_{67}$:$\beta$-$R_{68}$, $R_7$ is $\alpha$-H:$\beta$-H and $R_{10}$ is $\alpha$-$R_{107}$:$\beta$-$R_{108}$, where one of $R_{57}$ and $R_{58}$ is —H, $R_{107}$ and the other of $R_{57}$ and $R_{58}$ taken together are —(CH$_2$)$_2$—C(=$R_{33}$)—CH$_2$, where $R_{33}$ is as defined above, $R_{108}$ is —CH$_3$, where one of $R_{67}$ and $R_{68}$ is —H and the other is —H, —F, or $C_1$-$C_3$ alkyl;

(A-V) $R_6$ is $R_{69}$:$R_{610}$, $R_7$ is $R_{79}$:$R_{710}$, $R_{10}$ is $\alpha$-$R_{109}$:$R_{1010}$, where one of $R_{69}$ and $R_{610}$ is —H and the other taken together with one of $R_{79}$ and $R_{710}$ forms a second bond between $C_6$ and $C_7$, and the other of $R_{79}$ and $R_{710}$ is —H, $R_{1010}$ is —CH$_3$, $R_{109}$ and $R_5$ taken together are —(CH$_2$)$_2$—C(=$R_{33}$)—CH= or —CH=CH—CO—CH=, where $R_{33}$ is as defined above; where:

(C-I) $R_{11}$ is $\alpha$-$R_{111}$:$\beta$-$R_{112}$, where one of $R_{111}$ and $R_{112}$ is taken together with $R_9$ to form a second bond between $C_9$ and $C_{11}$ and the other of $R_{111}$ and $R_{112}$ is —H;

(C-II) $R_9$ is —Cl and $R_{11}$ is =O or $\alpha$-H:$\beta$-$R_{114}$ where $R_{114}$ is —Cl or —OH;

(C-III) $R_9$ is —H or —F and $R_{11}$ is =O or $\alpha$-$R_{115}$:$\beta$-$R_{116}$, where one of $R_{115}$ and $R_{116}$ is —H, and the other of $R_{115}$ and $R_{116}$ is —H, —OH or $C_1$-$C_{12}$ alkoxy;

(C-IV) $R_9$ is —H or —F and $R_{11}$ is $\alpha$-O-CO-$R_{117}$:$\beta$-H, where $R_{117}$ is
 (A) $C_1$-$C_3$ alkyl,
 (B) $C_1$-$C_{12}$ alkoxy,
 (C) furanyl,
 (D) —NR$_{122}$R$_{123}$, where on of $R_{122}$ and $R_{123}$ is —H, methyl or ethyl and the other is —H, $C_1$-$C_4$ alkyl or phenyl,
 (E) —X$_3$—X$_1$, where X$_3$ is —O— or a valence bond, where X$_1$ is phenyl optionally substituted with 1 through 2 —Cl, —Br, $C_1$-$C_3$ alkoxy, —COOH, —NH$_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethylenimino-, $C_2$-$C_4$ acylamino and —NH—CHO or with 1 —F or —CF$_3$; where:

(D-I) $R_{16}$ is $R_{161}$:$R_{162}$ and $R_{17}$ is $R_{171}$:$R_{172}$, where one of $R_{161}$ and $R_{162}$ is —H or —CH$_3$ and the other taken together with one of $R_{171}$ and $R_{172}$ forms a second bond between $C_{16}$ and $C_{17}$, and the other of $R_{171}$ and $R_{172}$ is —C(=Z)—(CH$_2$)$_n$—NR$_{21}$R$_{210}$, where Z is =O, =CH$_2$ or $R_{179}$:—H where $R_{179}$ is —H or —CH$_3$, where n is 0 through 6, where
 (A) $R_{21}$ is
  (1) —(CH$_2$)$_m$—NR$_{211}$—X$_2$, where m is 2, 3 or 4, where $R_{211}$ is —H or $C_1$-$C_3$ alkyl, where X$_2$ is:
   [A]
   (a) pyridin-2-, 3- or 4-yl or the N-oxide thereof optionally substituted by 1 or 2 $R_{212}$, being the same or different, where $R_{212}$ is
    (i) —F,
    (ii) —Cl,
    (iii) —Br,
    (iv) $C_1$-$C_5$ alkyl,
    (v) —CH$_2$—CH=CH$_2$,
    (vi) —X$_1$, where X$_1$ is as defined above,
    (vii) —NR$_{213}$R$_{213}$ where the $R_{213}$'s are the same or different and are —H, $C_1$-$C_3$ alkyl or —CH$_2$—CH=CH$_2$, (viii$\alpha$) *CH$_2$—(CH$_2$)$_q$—CH$_2$—N*— where the atoms marked with an asterisk (*) are bonded to each other resulting in the formation of a ring, where q is 1 through 5,
   (viii$\beta$) *CH$_2$—CH$_2$—(CH$_2$)$_c$—G—(CH$_2$)$_d$—CH$_2$—CH$_2$—N*— where the atoms marked with an asterisk (*) are bonded to each other resulting in the formation of a ring, where G is —O—, —S—, —SO—, —SO$_2$— or —NHR$_{214}$, where $R_{214}$ is —H, $C_1$-$C_3$ alkyl, or X$_1$ as defined above, where c and d are the same or different and are 0 through 2 with the proviso that the total number of ring carbon atoms is 4, 5 or 6, [a]
   (ix) 3-pyrrolin-1-yl, [b]
   (x) pyrrol-1-yl optionally substituted with $C_1$-$C_3$ alkyl, [c]
   (xi) piperidin-1-yl optionally substituted with 1 or 2 $C_1$-$C_3$ alkyl, [d]
   (xii) 1,2,3,6-tetrahydropyridin-1-yl, [e]
   (xiii) 1-hexamethyleneimino containing a 3- or 4- double bond or 3- and 5-double bonds, [f]
   (xiv) 1,4-dihydro-1-pyridinyl substituted in the 4 position by two $C_1$-$C_3$ alkyl being the same or different, [g]
   (xv) —OH,
   (xvi) $C_1$-$C_3$ alkoxy,
   (xvii) —NR$_{217}$—(CH$_2$)$_e$—Q where Q is 2-pyridinyl where $R_{217}$ is —H or $C_1$-$C_3$alkyl and e is 0 through 3 (1)
   (xviii) pyridin-2-, 3- or 4-yl,
  (b) 1,3,5-triazin-4-yl or the N-oxide thereof optionally substituted at the 2- and/or 6- position with $R_{212}$ is as defined above, (4)
  (c) pyrimidin-4-yl or the N-oxide thereof optionally substituted at the 2-and/or 6- position with $R_{212}$ is as defined above, (5)
  (d) pyrimidin-2-yl optionally substituted at 4- and/or 6- position with 1 or 2 $R_{212}$as is defined above, (6)
  (e) pyrazin-2-yl optionally substituted with 1 or 2 $R_{212}$ as is defined above, (7)
  (f) imidazol-2-yl optionally substituted in the 1 position with $C_1$-$C_3$ alkyl or —X$_1$, where X$_1$ is as defined above, and further optionally substituted with 1 or 2 $R_{212}$ as defined above, (8)
  (g) 1,3,4-triazol-2-yl optionally substituted in the 1 position with $C_1$-$C_3$ alkyl or —X$_1$, where X$_1$ is as defined above and further optionally substituted with $R_{212}$ as defined above, (9)
  (h) imidazol-4- or 5-yl optionally substituted in the 1 position with $C_1$-$C_3$ alkyl or —X$_1$, where X$_1$ is as defined above, and further optionally substituted with 1 or 2 $R_{212}$ as defined above, (10)
  (i) benzo[b] [thien-2-yl, (12a)
  (j) indol-2-yl, (12b)
  (k) benzo[b]thiazol-2-yl, (12c)
  (l) benzimidazol-2-yl, (12d)
  (m) 4-[2-[4-[2,6-bis(1-pyrrolidinyl)-4-pyrimidinyl]-1-piperazinyl]ethyl]-piperazinyl,
  (n) 1,2,4-triazin-3-yl optionally substituted at the 5- and/or 6-position with $R_{212}$ as is defined above, (14)
 (2) (1-piperazinyl)-($C_2$-$C_4$)alkyl optionally substituted in the 4-position with —X$_1$ or —X$_2$ as defined above, [B]
 (3) —X$_2$, as defined above, [O]

(4) —(CH$_2$)$_m$—X$_4$ where m is as defined above and where X$_4$ is
  (a) —O—CH$_2$CH$_2$—Y, where Y is C$_1$-C$_3$ alkylamino, di(C$_1$-C$_3$)alkylamino where the alkyl groups are the same or different, C$_3$-C$_6$ alkyleneimino, optionally substituted with 1 or 2 C$_1$-C$_3$ alkyl,
  (b) —NR$_{220}$CH$_2$CH$_2$—Y, where R$_{220}$ is —H or C$_1$-C$_3$ alkyl and Y is as defined above,
  (c) —(CH$_2$)$_g$—N(R$_{220}$)—X$_2$, where g is 2, 3 or 4, and where R$_{220}$ and X$_2$ are as defined above, [H]
(5) —(CH$_2$)$_m$—NR$_{222}$R$_{223}$, where R$_{222}$ is —H or C$_1$-C$_3$ alkyl and R$_{223}$ is —X$_1$ or —X$_2$ as defined above, or R$_{222}$ and R$_{223}$ are taken together with the attached nitrogen atom to form a saturated mono-nitrogen C$_3$-C$_6$ heterocyclic ring and where m is as defined above, [I]
(6) —(CHCH$_3$)$_b$—(CH$_2$)$_f$—R$_{224}$, where b is 0 and f is 1 through 3 or b is one and f is 0 through 3, where R$_{224}$ is phenyl substituted with 1 through 3 —OH, C$_1$-C$_3$ alkoxy, —NR$_{225}$R$_{226}$ where R$_{225}$ and R$_{226}$ are the same or different and are —H, C$_1$-C$_3$ alkyl or are taken together with the attached nitrogen atom to form a C$_4$-C$_7$ cyclicamino ring, [J]
(7) —(CH$_2$)$_i$—X$_2$, where i is 1 through 4 and X$_2$ is as defined above, [K]
(8) (1-piperazinyl)acetyl substituted in the 4-position by X$_2$ where X$_2$ is as defined above, [L]
(9) (1-piperazinyl)carbonylmethyl substituted in the 4- position by —X$_2$ where X$_2$ is as defined above, and [M]

(B) R$_{210}$ is
  (1) —H,
  (2) C$_1$-C$_3$ alkyl,
  (3) C$_5$-C$_7$ cycloalkyl,
  (4) —(CH$_2$)$_m$—NR$_{211}$—X$_2$, where m, R$_{211}$ and X$_2$ are as defined above, [A]
  (5) (1-piperazinyl)-(C$_2$-C$_4$)alkyl optionally substituted in the 4-position with —X$_1$ or —X$_2$ as defined above, [B]
  (6) —(CH$_2$)$_m$—X$_4$, where m and X$_4$ are as defined above, [H]
  (7) —(CH$_2$)$_m$—NR$_{222}$R$_{223}$, where m, R$_{222}$ and R$_{223}$ are as defined above, [I]
  (8) —(CHCH$_3$)$_b$—(CH$_2$)$_f$—R$_{224}$, where b, f and R$_{224}$ are as defined above, [J]

(C) R$_{21}$ and R$_{210}$ are taken together with the attached nitrogen atom to form a heterocyclic ring selected from the group consisting of
  (1) 2-(carboxy)-1-pyrrolidinyl optionally as the C$_1$-C$_3$ alkyl ester or as a pharmaceutically acceptable salt, [C-1]
  (2) 2-(carboxy)-1-piperidinyl optionally as the C$_1$-C$_3$ alkyl ester or as a pharmaceutically acceptable salt [C-2]
  (3) 2-(carboxy)-1-hexamethyleneimino optionally as the C$_1$-C$_3$ alkyl ester or as a pharmaceutically acceptable salt, [C-3]
  (4) 2-(carboxy)-1-heptamethyleneimino optionally as the C$_1$-C$_3$ alkyl ester or as a pharmaceutically acceptable salt, [C-4]
  (5) 1-piperazinyl substituted in the 4-position with R$_{228}$—CO—(CH$_2$)$_j$— where R$_{228}$ is —X$_1$, —NR$_{229}$X$_1$ and 2-furanyl, where R$_{229}$ is —H or C$_1$-C$_3$ alkyl, where j is 0 through 3 and X$_1$ is as defined above, [D]
  (6) 1-piperazinyl substituted in the 4-position with X$_2$—(CH$_2$)$_j$—, where X$_2$ and j are as defined above, [E]
  (7) 1-piperazinyl substituted in the 4-position with X$_1$—(CH$_2$)$_j$—, where X$_1$ and j are as defined above, [F]
  (8) 4-hydroxy-1-piperidinyl substituted in the 4-position with X$_1$ as defined above, [G]
  (9) 1-piperazinyl substituted in the 4-position with X$_2$—NR$_{229}$—CO—(CH$_2$)$_i$—, where X$_2$, R$_{229}$ and i are as defined above; [N]

(D-II) R$_{16}$ is α-R$_{163}$:β-R$_{164}$ where one of R$_{163}$ and R$_{164}$ is —H and the other is —H, —F, —CH$_3$ or —OH, and R$_{17}$ is —CH—(CH$_2$)$_p$—NR$_{21}$R$_{210}$, where p is 1 or 2, where R$_{21}$ and R$_{210}$ are as defined above.

(D-III) R$_{16}$ is α-R$_{165}$:β-R$_{166}$ and R$_{17}$ is α-R$_{175}$:β-R$_{176}$, where R$_{165}$ is —H, —OH, —F or —CH$_3$ and R$_{166}$ is —H, —OH, —F, or —CH$_3$, with the proviso that at least one of R$_{165}$ and R$_{166}$ is —H, where R$_{175}$ is —H, —OH, —CH$_3$, —CH$_2$CH$_3$, C$_2$-C$_7$ alkanoyloxy or —O—CO—X$_1$, where X$_1$ is as defined above, and where R$_{176}$ is —C(=Z)—(CH$_2$)n—NR$_{21}$R$_{210}$, where Z, n, R$_{21}$ and R$_{210}$ are as defined above;

(D-IV) the 16,17-acetonide of a compound where R$_{165}$ is —OH, R$_{166}$ is —H, R$_{175}$ is —OH and R$_{176}$ is —C(=Z)—(CH$_2$)$_n$—NR$_{21}$R$_{210}$, where Z, n, —R$_{21}$ and R$_{210}$ are as defined above;

and pharmaceutically acceptable salts thereof, and hydrates and solvates thereof; with the following overall provisos that:

(I) one of R$_{161}$ or R$_{162}$ is taken together with one of R$_{171}$ or R$_{172}$ to form a second bond between C$_{16}$ and C$_{17}$, only when R$_{10}$ is α-R$_{101}$:β-R$_{102}$, α-R$_{103}$:β-R$_{104}$, α-R$_{107}$:β-R$_{108}$ or α-R$_{109}$:β-R$_{1010}$, (II) R$_{17}$ is —CH—(CH$_2$)$_p$—NR$_{21}$R$_{210}$, only when R$_{10}$ is α-R$_{101}$:β-R$_{102}$, α-R$_{103}$:β-R$_{104}$, α-R$_{107}$:β-R$_{108}$ or α-R$_{109}$:β-R$_{1010}$, (III) R$_5$ and R$_{10}$ taken together are =CH—CH=C(OR$_3$)—CH=, only when R$_{17}$ is α-R$_{175}$:β-R$_{176}$ or the 16,17-acetonide of a compound where R$_{16}$ is α-OH:β-H and R$_{17}$ is α-OH:β-C(=Z)—(CH$_2$)$_n$—NR$_{21}$R$_{210}$, and (IV) R$_5$ is α-R$_{57}$:β-R$_{58}$, only when R$_{17}$ is α-R$_{175}$:β-R$_{176}$ or α-OH:β-C—(=Z)—(CH$_2$)$_n$—NR$_{21}$R$_{210}$, or the 16,17-acetonide thereof.

More prefered are the C$_{21}$ aminosteroids of formula XI, especially those which inhibit lipid peroxidation. Most preferred are the 21-[4-(substituted-4-pyrimidinyl)-1-piperizinyl]-steroids, such as U-74006 (21-[4-(2,6-dipyrrolidinyl-4-pyrimidinyl)-1-piperazinyl]-16α-methylpregna-1,4,9(11)-triene-3,20-dione, and the 21-[4-(substituted-2-pyridinyl)-1-piperazinyl]-steroids, such as U-74500 (21-[4-[5,6-bis(diethylamino)-2-pyridinyl]-1-piperazinyl]-16α-methylpregna-1,4,9(11)-triene-3,20-dione and U-75472 (21-[4-(3-ethylamino-2-pyridinyl)-1-piperazinyl]-16α-methylpregna-1,4,9(11)-triene-3,20-dione, all, when in the unformulated state, preferably as a solid, preferably crystalline, preferably relatively non-hygroscopic and pharmaceutically acceptable salts, such as the methanesulfonate salt of U74006 (U-74006F), the hydrochloride of U-74500 (U-74500A), and the hydrochloride or maleic acid salt of U-75412 (U-75412A and U-75412E, resp.) The following are illustrative structures.

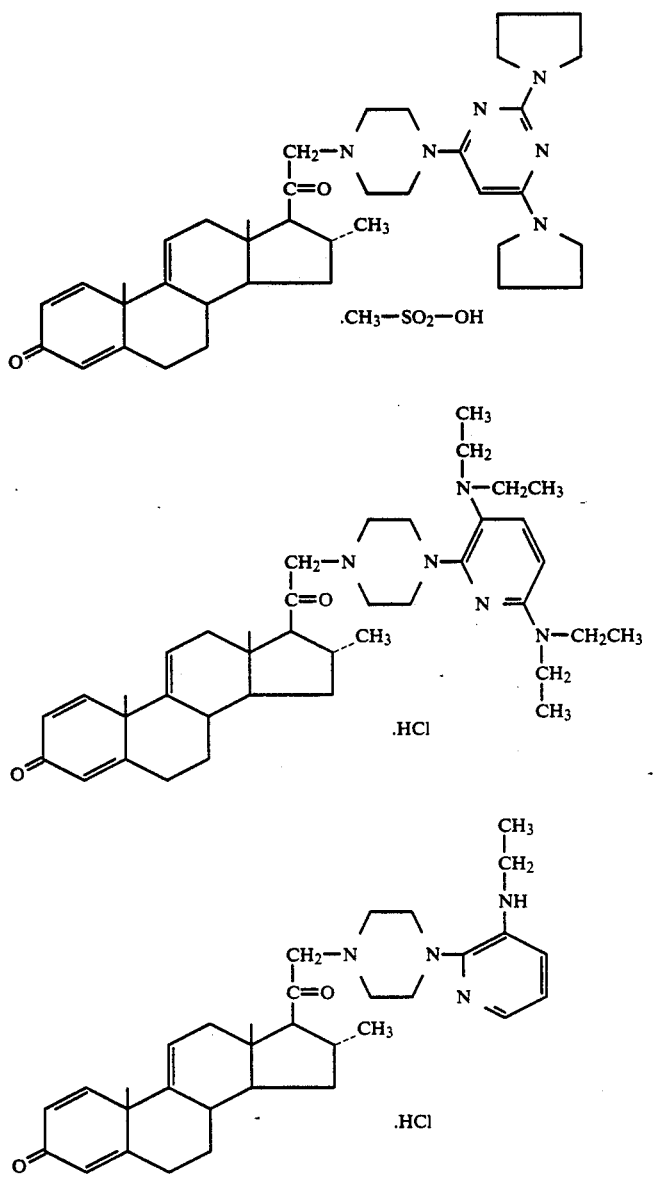

The above preferred amino steroids are all exemplified as 21-substituted-16α-methylpregna-1,4,9(11)-triene-3,20-diones. However, the steroidal portion of these may be modified without substantially altering their preferred nature. Thus a class of preferred $C_{21}$ amino substituted steroids may be represented by the formula I, below

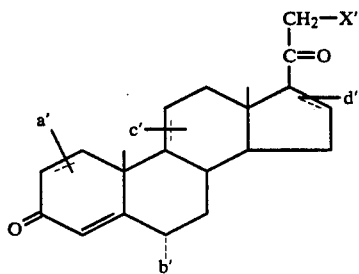

(I)

where:

a' is selected from the group 1,2-dihydro (saturated) and 1,2-dehydro (1,2-double-bond);

b' is selected from the group 6α-H, 6α-methyl and 6α-fluoro;

c' is selected from the group 9,11-dihydro (saturated), 9(11)-dehydro (double-bond), 9α-H-11α-OH-11β-H, 9α-H-11β-OH-11α-H, 9α-H-11-keto, 9α-F-11β-OH-11α-H and 9α-F-11-keto;

d' is selected from the group 16α-methyl-16β-H-17α-H, 16β-methyl-16α-H-17α-H, 16-H$_2$-17α-H, 16-H-16,17-dehydro (double-bond), and 16-methyl-16,17-dehydro. Less preferably, a 17α-OH group can be present instead of 17α-H when d' is not 16-H-16,17-dehydro or 16-methyl-16,17-dehydro; and where:

X' is selected from the complex 21-amino substituents X1' and X2' where

X1' is

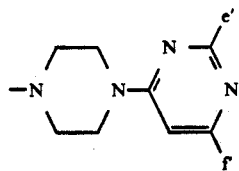

and

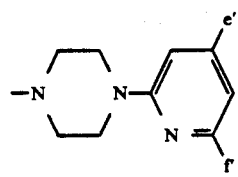

X2' is
where e' and f' may be the same or different and are selected from the group: H, NHR1' and NR1'R2', where R1' and R2' are C1 to C3 lower alkyl or R1' and R2', taken together with N, constitute a heterocyclic ring; preferably 1-ethyleneimino, 1-trimethyleneimino, 1-pyrrolidinyl, 1-piperidinyl, 1-morpholinyl and 1-(4-methyl)-piperazinyl.

It is within the ability of those skilled in the art to determine without undue experimentation which of the foregoing aminosteroids will function as antioxidant agents. The publication WO 87/01706 indicates that arachidonic acid $LD_{50}$ test of Kohler, Thrombosis Res., 9,67 (1976) identifies compounds which are antioxidants, and the publication also references Pryor in Methods of Enzymology 105,293 (1984) for another method useful for determining which particular compounds inhibit lipid peroxidation.

By formulating the above-described amino-substituted steroids into an appropriate inert vehicle or carrier, it is possible to prevent or treat ophthalmic diseases or disorders such as cataracts, glaucoma or the risk of glaucoma associated with significantly elevated intraocular pressure, inflammatory eye disease, retinal eye disease, intraocular pressure rise due to uveitus, post-infarct ambolus, traumatic eye injury (such as blunt trauma, compression injury, hyphema, surgical trauma, etc.), neovascular or ischemic eye disease (conditions in the eye involving ischemia such as corneal edema from prolonged wearing of contact lenses and the like), bullous keratitis, dry eye including keratitis sicca, alkali burn and conditions arising from transplantation of a corneal graft or transplantation of ocular cells.

Topical administration is preferable when the target of the treatment is located in or near the anterior chamber of the eye. By contrast, because the flow of aqueous humor is from the ciliary body (behind the iris) forward towards the cornea before it exits through the trabecular meshwork and Schlemm's canal, penetration of drugs to the back of the eye when administered topically to the front of the eye occurs with some difficulty. It is therefore often more effective to administer drugs intended for the treatment of uveal and retinal diseases by the systemic route where access to the eye occurs through the choroid plexus, or by the intravitreal route. Some of the more severe eye diseases affect those targets which are difficult to treat effectively by the topical route and they can be associated with markedly impaired vision or blindness. Accordingly, the topical route is preferred for convenience of individual patient self-administration, and the intraocular and systemic routes are preferred for surgical and presurgical administration.

In order to maintain an ocularly adequate therapeutic level of drug in the back of the eye where surgery is not involved, or has been concluded, the present invention also contemplates the treatment of an ophthalmic disease by administration of a therapeutically effective amount of amino-substituted steroid antioxidant agent (including salts, hydrates, or solvates), in a suitable carrier, by oral, intramuscular and intravenous routes, in addition to the convenient topical route or by intraocular injection.

In general, ophthalmic formulations suitable for topical and intraocular administration may be formulated and administered in accordance with techniques known to persons skilled in the art. Because the amino-substituted steroids are themselves capable of oxidative degradation, it is desirable that the ophthalmic formulations including them be constituted to avoid oxidation and excessive exposure to light. The formulations are preferably prepared in an anaerobic environment by making all formulations under an inert gas. The finished formulations are preferably stored in opaque or brown containers to protect them from light exposure, and under an inert atmosphere.

Aqueous polymeric solutions, aqueous suspensions, ointments, and gels are preferably used for topical formulations. The aqueous formulations may also contain liposomes for creating a reservoir of dissolved amino-substituted steroid therapeutic agent for contact with the tear film. Particularly preferred among topical formulations are gels, which enhance pre-corneal retention and protect the amino-substituted steroids from degradation without the inconvenience and impairment of vision associated with ointments.

Topical formulations should generally include between 0.01 and 10% by weight, preferably between 0.1 and 5% by weight, of the amino-substituted steroid therapeutic agent in a suitable polymeric carrier. Suitable polymeric carriers include lightly crosslinked carboxy-containing polymers (such as polycarbophil), dextran, cellulose derivatives, polyethyleneglycol 400 and other polymeric demulcents.

Other additives which are desirably included in the topical formulations include sodium chloride, EDTA (disodium edetate), surfactants, and preservatives like BAK (benzalkonium chloride). Administration of the formulation to the eye will typically be carried out between one and four times a day, depending on the particular problem being treated.

Formulations suitable for ocular injection fall into two categories. For subconjunctival injection, the formulations should generally include between 0.01 and 5% by weight, preferably between 0.05 and 2% by weight of amino-substituted steroid therapeutic agent. Any suitable carriers may be employed, preferably polymeric carriers such as dextran or polysorbate 80. Other additives which desirably may be included in the formulations are disodium edetate and sodium sulfite. To administer the formulations to the eye, the drug formulations will be slowly injected into the bulbar conjunctiva of the eye. For intracameral or intravitreal injections, the suitable formulation should include phosphate buffered saline, citrate buffered saline, chrondroitin sulfate, or a polymeric carrier such as sodium hyaluronate (or hyaluronic acid), purified polyacrylamide or polysorbate 80. Other additives which are desirably included in the ocularly injectable formulations are sodium chloride, sodium hydroxide and hydrogen chloride, where sodium hydroxide and hydrogen chloride are used for adjustment of pH. Typically, the formulations contain between 0.001 and 1%, preferably between 0.005 and 0.15% especially when in solution, by weight of the amino-substituted steroid therapeutic agent. When the agent is substantially in solution, it is rapidly available to exert its therapeutic function and lower concentrations may therefore be administered to achieve effective levels without causing tissue intolerance. When the agent is substantially in suspension, higher concentrations may be administered to achieve a sustained effective level, again without causing tissue intolerance. Hence, with solutions, lower concentrations are employed to avoid local tissue damage. With a suspension, higher concentrations are employed because a smaller dissolved amount is introduced for immediate activity.

To administer the formulations intravitreally to the eye, the drug formulation will be injected through the sclera layer of the eye into the vitreous cavity. To administer the formulations intracamerally, the drug formulations will be injected through the cornea into the anterior chamber of the eye.

Formulations for intravenous, intramuscular, and oral administration are likewise prepared in accordance with techniques well known to persons skilled in the art. Intravenous formulations for ophthalmic use in methods of the present invention may be prior art formulations used for other purposes and will typically include between 0.05 and 5.0% by weight and preferably between 0.1 and 1.0% by weight of the amino-substituted steroid therapeutic agent. Suitable carriers for such intravenous amino-substituted steroid formulations are those well known to persons skilled in the art such as citrate buffer, borate buffer and others. Other additives which may be desirably added to intravenous formulations include sodium chloride, sodium sulfite, disodium edetate and benzyl alcohol. Alternative formulations suitable for intravenous administration include carriers such as lipid emulsions containing the amino-substituted steroid and unilamellar or multilamellar liposome formulations of the amino substituted steroid. To administer the intravenous formulations for treatment of the eye, the drug formulations are preferably dose injected or infused into a major vein (e.g., in the arm area), or introduced by continuous intravenous drip.

Intramuscular formulations will typically include between 0.01 and 10.0% by weight and preferably between 0.5 and 5.0% by weight of the amino-substituted steroid therapeutic agent. Suitable adjuvants in aqueous solution or suspension for intramuscular lazaroid formulations are those well known to persons skilled in the art such as polysorbate 80, methyl cellulose, and other demulcents. Other additives desirably added to intramuscular formulations include sodium chloride and sodium bisulfite. To administer the intramuscular formulations for treatment of the eye, the drug formulations will be injected for example into the upper outer quadrant of the gluteal muscle.

Finally, formulations suitable for oral administration will include both liquid formulations (aqueous solutions, aqueous suspension, elixirs, and the like) and solid dosage forms, both containing additives and adjuvants well known to persons skilled in the art. Aqueous solutions and suspensions for liquid oral administration will typically contain between 0.05 and 5% by weight and preferably between 0.1 and 2.0% by weight of the amino-substituted steroid therapeutic agent. Suitable adjuvants may be used as carriers to provide wetability and stability such as propylene glycol, lightly crosslinked carboxy-containing polymers such as polycarbophil, ethyl cellulose, hydroxypropyl cellulose and methyl cellulose. Other additives, including sodium edetate, methyl and propyl parabens, flavoring agents and colorants may be employed if desired. Solid dosage forms for oral administration may also be prepared as capsules, caplets or tablets with the aid of fillers, lubricants and stabilizers. To administer oral formulations for treatment of the eye, the drug is swallowed in solid dosage form or as a solution or suspension.

The following examples are given for illustrative purposes only and should in no way be construed as limiting the subject matter presently disclosed and claimed.

EXAMPLE 1

Compositions of matter taught in the prior art containing U-74006F, U-74500A or U-75412A suitable for intravenous administration are prepared for administration in a method of the present invention. Ten grams of tirilazad methanesulfonate (U-74006F), the hydrochloride salt of U-74500 (U-74500A), or the hydrochloride salt of U-75412 (U-75412A), all of which salts are described by Braughler et al, Biochemical Pharmacology 37:3853-360, are added slowly with stirring to 950 ml of 0.05N hydrochloric acid. The total weight is adjusted to 1000 g by the addition of 0.05N hydrochloric acid and the solution is sterile filtered and filled into sterile ampoules containing 10 ml each of the aminosteroid antioxidant solution, 10 mg/g, or 1.0% by weight. In accordance with the present invention, to prevent or treat an ophthalmic disease or disorder, this material is administered intravenously by injection, by infusion, or, following addition to isotonic saline, by slow IV drip. The preparation is preferably administered intravenously to a patient by slow IV drip one hour before surgery to remove a cataract. It is given to reduce any traumatic side effects, such as macular edema, from intraocular lens surgery, with the aminosteroid therapeutic agent being introduced in an ophthalmically effective amount to arrest processes damaging to the eye (particularly oxidation processes) of a human or other animal that is subject to intraocular damage and in need of improved visual function or prevention of its loss from such damage.

EXAMPLE 2

Compositions of matter taught in the prior art containing U-74006F, U-74500A or U-75412A suitable for intravenous administration are prepared for administration in a method of the present invention. To 900 ml of water for injection is added 20 millimoles of citric acid, 3 millimoles of sodium citrate and 8 millimoles of sodium chloride. To the thus obtained solution of citrate buffered saline is slowly added 10 grams of the aminosteroid antioxidant agent with stirring. The total weight is adjusted to 1000 g by addition of water. The solution of the agent in citrate buffered saline is sterile filtered and filled into sterile ampoules or vials each containing 10 ml of the solution, 10 mg/g, or 1.0% by weight. In accordance with the present invention this material is administered as in Example I.

EXAMPLE 3

Compositions of matter taught in the prior art containing U-74006F, U-74500A or U-75412A suitable for oral administration are prepared for administration in a method of the present invention. Following standard procedures well known in the pharmaceutical art, capsules, caplets and tablets containing 1, 5, 10, 25, 50 and 100 mg of the aminosteroid antioxidant agent are prepared. These capsules, caplets and tablets are suitable for oral administration. In their place, there can also be prepared by standard methods an aqueous solution or suspension of the solution containing 1, 5, 10 and 25 mg/g, or 0.1, 0.5, 1.0, and 2.5% by weight respectively. In accordance with the present invention, to prevent or treat an ophthalmic disease or disorder, the capsules, caplets, tablets or liquids are administered orally, with the aminosteroid therapeutic agent being introduced in an ophthalmically effective amount to arrest processes damaging to the eye (particularly oxidation processes) of a human or other animal that is subject to intraocular damage and in need of improved visual function or prevention of its loss from such damage.

EXAMPLE 4

Compositions of matter are prepared containing U-74006F, U-74500A or U-75412A suitable for intramuscular administration in a method of the present invention. Sterile suspensions of 20,000 to 30,000 cps viscosity are prepared containing 25, 50 and 100 mg (2.5, 5.0 and 10.0% by weight) of the aminosteroid antioxidant agent in a polysorbate 80, methyl cellulose, or other polymeric demulcent vehicle. The technique for preparing a suspension and adjusting viscosity is well known in the pharmaceutical art. In accordance with the present invention, to prevent or treat an ophthalmic disease or disorder these compositions are given intramuscularly, e.g., through injection into the outer quadrant of the gluteal region, with the aminosteroid therapeutic agent being introduced in an ophthalmically effective amount to arrest processes damaging to the eye (particularly oxidation processes) of a human or other animal that is subject to intraocular damage and in need of improved visual function or prevention of its loss from such damage.

EXAMPLE 5

Compositions of matter according to the present invention are prepared containing U-74006F, U-74500A or U-75412A suitable for topical administration to the eye in a method of the present invention. A formulation of viscosity of 5,000 cps or greater is prepared by adding 40 g of propylene glycol, 2 g of polyethylene glycol 4000, 3 g of hydroxypropyl cellulose, and 0.1 g EDTA to 50 g of intravenous grade water. To this mixture, 0.15 g of the aminosteroid antioxidant agent is added as a powder or included in a liposome, and the total weight is brought to 100 g with water. The agent is dissolved or dispersed by overhead mixing for 30 minutes, and the 0.15% formulation is sterilized for 30 minutes at 121° C. To prevent or treat an ophthalmic disease or disorder, the composition is topically administered to the eye one to four times a day, with the aminosteroid therapeutic agent being introduced in an ophthalmically effective amount to arrest processes damaging to the eye (particularly oxidation processes) of a human or other animal that is subject to intraocular damage and in need of improved visual function or prevention of its loss from such damage.

EXAMPLE 6

Otherwise following the procedure of example 5, about 100 mg of benzalkonium chloride is added prior to sterilization, and there is obtained a sterile, preserved ophthalmic formulation that is sterile filled into suitable dropper vials to provide a multi-dose eyedrop composition. In place of benzalkonium chloride, there may be substituted an effective amount of other approved preservatives, such as chlorobutanol, sorbic acid, cetrimonium bromide and the like. Topical administration of this 0.15% formulation to the surface of the eye is as in Example 5.

EXAMPLE 7

Bioadhesive compositions of matter in accordance with the present invention are prepared containing U-74006F, U-74500A or U-75412A suitable for topical administration to the eye in a method of the present invention. A formulation of 5,000 cps viscosity or greater is prepared by suspending 1 g of Carbopol 976, a polycarbophil, in 95 g of intravenous grade water. The solution is mixed by overhead stirring for 1 hour. To this solution 0.55 g of sodium chloride and 0.08 g of EDTA are added and stirring is continued for 5 minutes. The pH of the solution is adjusted to 6.0 by dropwise addition of 1N sodium hydroxide. This forms a gel. To this formulation is added 0.15 g of the aminosteroid therapeutic agent and stirring is continued for 30 minutes. The total weight is adjusted to 100 g by addition of water and the composition is sterilized at 121° C. for 30 minutes. This 0.15% formulation is then applied topically as in Example 5.

EXAMPLE 8

Compositions in accordance with the present invention and similar to those of Example 7 are prepared by following the procedure of Example 7, but adding 100 mg of the preservative benzalkonium chloride prior to sterilization. There is produced a preserved formulation suitable for sterile filling into multidose containers. The formulation is applied topically as in Example 5.

EXAMPLE 9

Compositions of matter taught in the prior art are prepared containing U-74006F, U-74500A or 75412A suitable for intraocular administration into the anterior chamber before, after, and during a surgical procedure in a method of the present invention. A saline solution is prepared by dissolving 0.9 g of sodium chloride in 98 g of intravenous grade water. To this solution, 0.005 g of the aminosteroid therapeutic agent is added as a powder or in a lipid emulsion, unilamellar liposome or multilamellar liposome, and is dissolved or dispersed by stirring. The pH is adjusted to 7.4 with 1N sodium hydroxide and the total weight is adjusted to 100 g by addition of water. The mixture is sterilized at 121° C. for 30 minutes and filled into amber ampoules under a nitrogen atmosphere. The 0.005% composition is then administered intracamerally by injection through the cornea into the anterior chamber of the eye before, during or after surgical procedures, with the aminosteroid therapeutic agent being introduced in an ophthalmically effective amount to arrest processes damaging to the eye (particularly oxidation processes) of a human or other animal that is subject to intraocular damage and in need of improved visual function or prevention of its loss from such damage.

EXAMPLE 10

Compositions in accordance with the present invention are prepared by adding to the solution in Example 9, 1.0 g of sodium hyaluronate and a total of 0.05 g of the agent (a higher amount than in Example 9) which is mixed thoroughly before the addition of water to 100 g. The suspension is administered in accordance with the present invention as in Example 9.

EXAMPLE 11

Compositions of matter in accordance with the present invention are prepared containing U-74006F, U-74500A or U-75412A suitable for intraocular application by subconjunctival administration according to the present invention. In 95 g of intravenous grade water is dissolved 0.5 g of methyl cellulose, 0.75 g of polysorbate 80 and 0.1 g of sodium bisulfite. To this formulation 0.12 g of the aminosteroid therapeutic agent is added with stirring for 20 to 30 minutes to make a suspension. The pH of solution is adjusted to 7.4 using 1N sodium hydroxide while overhead stirring of the formulation is continued. After adjusting the total weight to 100 g with water, this preparation is then steam sterilized at 121° C. for 30 minutes, and is then transferred aseptically into sterile ampoules for injection. In accordance with the present invention, to prevent or treat an ophthalmic disease or disorder, the composition is administered by subconjunctival injection, with the aminosteroid therapeutic agent being introduced in an ophthalmically effective amount to arrest processes damaging to the eye (particularly oxidation processes) of a human or other animal that is subject to intraocular damage and in need of improved visual function or prevention of its loss from such damage.

EXAMPLE 12

Compositions of matter taught in the prior art are prepared containing U-74006F suitable for intravitreal administration in accordance with the present invention. Ten grams of U-74006F is added slowly with stirring to 950 mls pure water containing 20 millimoles of citric acid under an inert atmosphere. Three millimoles of sodium citrate and 8 millimoles of sodium chloride are added and stirring is continued until a clear solution is obtained. The total weight is then adjusted to 1000 g by addition of water. The thus obtained solution is sterile filtered and, under sterile conditions, is added to unit dose containers, each container containing 0.2 ml, to provide about 5000 units of a 1% composition. In accordance with the present invention, to prevent or treat an ophthalmic disease or disorder, this composition is administered by injection through the sclera layer of the eye into the vitreous cavity, with the aminosteroid therapeutic agent being introduced in an ophthalmically effective amount to arrest processes damaging to the eye (particularly oxidation processes) of a human or other animal that is subject to intraocular damage and in need of improved visual function or prevention of its loss from such damage.

EXAMPLE 13

Any or all of the foregoing Examples 1-12 are repeated, substituting or adding one or more other aminosteroid therapeutic agents selected from the $C_{20}$ through $C_{26}$ aminosteroids of the formula XI structure (especially those which exhibit antioxidant functions), and pharmaceutically acceptable salts, hydrates, or solvates thereof, keeping the total amount of agent as in Examples 1-12. One such agent is U-77372E. The structure of U-77372E, 21-[4-(4,6-bis-(2-pyridinyl) triazin-2-yl)-1]-16α-methylpregra-1,4,9(11)-triene-3,20-dione methanesulfonate, may be obtained from the description in Braughler et al, Biochemical Pharmocology 37:3856, 1988.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method of arresting processes damaging to the eye, comprising:
administering, by intraocular injection, to the eye tissue of a human or other animal that is subject to intraocular damage, and in need of improved visual function or prevention of its loss from such damage, a formulation containing a therapeutically effective amount between .001 and 5% by weight of an amino-substituted steroid therapeutic agent selected from the $C_{20}$ through $C_{26}$ aminosteroids of the following formula XI:

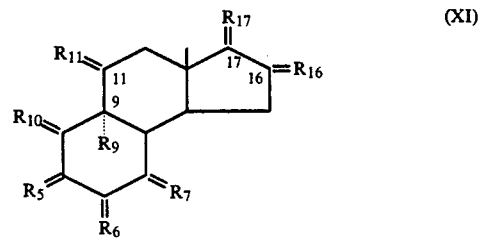

where:
(A-I) $R_6$ is α-$R_{61}$:β-$R_{62}$, $R_{10}$ is α-$R_{101}$:β-$R_{102}$ and $R_7$ is α-H:β-H, where one of $R_{61}$ and $R_{62}$ is —H, and the other is —H, —F, or $C_1$-$C_3$ alkyl, $R_{102}$ is —$CH_3$, $R_{101}$ and $R_5$ taken together are —$(CH_2)_2$—C(—$R_{33}$)—CH= or —CH—CH—CO—CH=, where $R_{33}$ is =O or α-H:β-$OR_{34}$ or α-$OR_{34}$:β-H, where $R_{34}$ is —H, —P(=O)(OH)$_2$, —CO—$CH_3$, —CO—$C_2H_5$, —CO—$C_6H_5$, —CO—O—$CH_3$ or —CO—O—$C_2H_5$;

(A-II) $R_5$ is α-$R_{53}$:β-$R_{54}$, $R_6$ is α-$R_{63}$:β-$R_{64}$, $R_{10}$ is α-$R_{103}$:β-$R_{104}$ and $R_7$ is α-H:β-H, where one of $R_{63}$ and $R_{64}$ is —H, and the other taken together with one of $R_{53}$ and $R_{54}$ forms a second bond between $C_5$ and $C_6$, $R_{104}$ is —$CH_3$, $R_{103}$ and the other of $R_{53}$ and $R_{54}$ taken together are —$(CH_2)_2$—C(H)(OH)—$CH_2$— or —$(CH_2)_2$—C[H][OP(=O)—(OH)$_2$]—$CH_2$—;

(A-III) $R_{10}$ and $R_5$ taken together are =CH—CH=C(OR$_3$)—CH= where $R_3$ is —H, —P(=O)(OH)$_2$, $C_1$-$C_3$ alkyl, —CO—H, $C_2$-$C_4$ alkanoyl or benzyl, $R_6$ is α-$R_{65}$:β-$R_{66}$ where one of $R_{65}$ and $R_{66}$ is —H, and the other is —H, —F, or $C_1$-$C_3$ alkyl and $R_7$ is α-H:β-H;

(A-IV) $R_5$ is α-$R_{57}$:β-$R_{58}$, $R_6$ is α-$R_{67}$:β-$R_{68}$, $R_7$ is α-H:β-H and $R_{10}$ is α-$R_{107}$:β-$R_{108}$, where one of $R_{57}$ and $R_{58}$ is —H, $R_{107}$ and the other of $R_{57}$ and $R_{58}$ taken together are —$(CH_2)_2$—C(=$R_{33}$)—$CH_2$, where $R_{33}$ is as defined above, $R_{108}$ is $-CH_3$, where one of $R_{67}$ and $R_{68}$ is $-H$ and the other is $-H$, $-F$, or $C_1-C_3$ alkyl;

(A-V) $R_6$ is $R_{69}$:$R_{610}$, $R_7$ is $R_{79}$:$R_{710}$, $R_{10}$ is $\alpha$-$R_{109}$:$R_{1010}$, where one of $R_{69}$ and $R_{610}$ is $-H$ and the other taken together with one of $R_{79}$ and $R_{710}$ forms a second bond between $C_6$ and $C_7$, and the other of $R_{79}$ and $R_{710}$ is $-H$, $R_{1010}$ is $-CH_3$, $R_{109}$ and $R_5$ taken together are $-(CH_2)_2-C(=R_{33})-CH=$ or $-CH=CH-CO-CH=$, where $R_{33}$ is as defined above; where:

(C-I) $R_{11}$ is $\alpha$-$R_{111}$:$\beta$-$R_{112}$, where one of $R_{111}$ and $R_{112}$ is taken together with $R_9$ to form a second bond between $C_9$ and $C_{11}$ and the other of $R_{111}$ and $R_{112}$ is $-H$;

(C-II) $R_9$ is $-Cl$ and $R_{11}$ is $=O$ or $\alpha$-$H$:$\beta$-$R_{114}$ where $R_{114}$ is $-Cl$ or $-OH$;

(C-III) $R_9$ is $-H$ or $-F$ and $R_{11}$ is $=O$ or $\alpha$-$R_{115}$:$\beta$-$R_{116}$, where one of $R_{115}$ and $R_{116}$ is $-H$, and the other of $R_{115}$ and $R_{116}$ is $-H$, $-OH$ or $C_1-C_{12}$ alkoxy;

(C-IV) $R_9$ is $-H$ or $-F$ and $R_{11}$ is $\alpha$-$O-CO-R_{117}$:$\beta$-$H$, where $R_{117}$ is
  (A) $C_1-C_3$ alkyl,
  (B) $C_1-C_{12}$ alkoxy,
  (C) furanyl,
  (D) $-NR_{122}R_{123}$, where one of $R_{122}$ and $R_{123}$ is $-H$, methyl or ethyl and the other is $-H$, $C_1-C_4$ alkyl or phenyl,
  (E) $-X_3-X_1$, where $X_3$ is $-O-$ or a valence bond, where $X_1$ is phenyl optionally substituted with 1 through 2 $-Cl$, $-Br$, $C_1-C_3$ alkoxy, $-COOH$, $-NH_2$, $C_1-C_3$ alkylamino, di($C_1-C_3$)alkylamino, where the alkyl groups are the same or different, 1-pyrrolidinyl-, 1-piperidinyl, 1-hexamethylenimino-, 1-heptamethylenimino-, $C_2-C_4$ acylamino and $-NH-CHO$ or with 1 $-F$ or $-CF_3$; where:

(D-I) $R_{16}$ is $R_{161}$:$R_{162}$ and $R_{17}$ is $R_{171}$:$R_{172}$, where one of $R_{161}$ and $R_{162}$ is $-H$ or $-CH_3$ and the other taken together with one of $R_{171}$ and $R_{172}$ forms a second bond between $C_{16}$ and $C_{17}$, and the other of $R_{171}$ and $R_{172}$ is $-C(=Z)-(CH_2)_n-NR_{21}R_{210}$, where Z is $=O$, $=CH_2$ or $R_{179}$:$-H$ where $R_{179}$ is $-H$ or $-CH_3$, where n is 0 through 6, where
(A) $R_{21}$ is
  (1) $-(CH_2)_m-NR_{211}-X_2$, where m is 2, 3 or 4, where $R_{211}$ is $-H$ or $C_1-C_3$ alkyl, where $X_2$ is:
    (a) pyridin-2-, 3- or 4-yl or the N-oxide thereof optionally substituted by 1 or 2 $R_{212}$, being the same or different, where $R_{212}$ is
      (i) $-F$,
      (ii) $-Cl$,
      (iii) $-Br$,
      (iv) $C_1-C_5$ alkyl,
      (v) $-CH_2-CH=CH_2$,
      (vi) $-X_1$, where $X_1$ is as defined above,
      (vii) $-NR_{213}R_{213}$ where the $R_{213}$'s are the same or different and are $-H$, $C_1-C_3$ alkyl or $-CH_2-CH=CH_2$,
      (viii$\alpha$) *$CH_2-(CH_2)_q-CH_2-N$*—where the atoms marked with an asterisk (*) are bonded to each other resulting in the formation of a ring, where q is 1 through 5,
      (viii$\beta$) *$CH_2-CH_2-(CH_2)_c-G-(CH_2)_d-CH_2-CH_2-N$*—where the atoms marked with an asterisk (*) are bonded to each other resulting in the formation of a ring, where G is $-O-$, $-S-$, $-SO-$, $-SO_2-$ or $-NHR_{214}$, where $R_{214}$ is $-H$, $C_1-C_3$ alkyl, or $X_1$ as defined above, where c and d are the same or different and are 0 through 2 with the proviso that the total number of ring carbon atoms is 4, 5 or 6, [a]
      (ix) 3-pyrrolin-1-yl, [b]
      (x) pyrrol-1-yl optionally substituted with $C_1-C_3$ alkyl,
      (xi) piperidin-1-yl optionally substituted with 1 or 2 $C_1-C_3$ alkyl,
      (xii) 1,2,3,6-tetrahydropyridin-1-yl, [e]
      (xiii) 1-hexamethyleneimino containing a 3- or 4- double bond or 3- and 5- double bonds, [f]
      (xiv) 1,4-dihydro-1-pyridinyl substituted in the 4 position by two $C_1-C_3$ alkyl being the same or different, [g]
      (xv) $-OH$,
      (xvi) $C_1-C_3$ alkoxy,
      (xvii) $-NR_{217}-(CH_2)_e-Q$ where Q is 2-pyridinyl where $R_{217}$ is $-H$ or $C_1-C_3$ alkyl and e is 0 through 3 (1)
      (xviii) pyridin-2-, 3- or 4-yl,
    (b) 1,3,5-triazin-4-yl or the N-oxide thereof optionally substituted at the 2- and/or 6-position with $R_{212}$ is as defined above, (4)
    (c) pyrimidin-4-yl or the N-oxide thereof optionally substituted at the 2- and/or 6- position with $R_{212}$ is as defined above, (5)
    (d) pyrimidin-2-yl optionally substituted at 4- and/or 6-position with 1 or 2 $R_{212}$ as is defined above, (6)
    (e) pyrazin-2-yl optionally substituted with 1 or 2 $R_{212}$ as is defined above, (7)
    (f) imidazol-2-yl optionally substituted in the 1 position with $C_1-C_3$ alkyl or $-X_1$, where $X_1$ is as defined above, and further optionally substituted with 1 or 2 $R_{212}$ as defined above, (8)
    (g) 1,3,4-triazol-2-yl optionally substituted in the 1 position with $C_1-C_3$ alkyl or $-X_1$, where $X_1$ is as defined above, and further optionally substituted with $R_{212}$ as defined above, (9)
    (h) imidazol-4- or 5-yl optionally substituted in the 1 position with $C_1-C_3$ alkyl or $-X_1$, where $X_1$ is as defined above, and further optionally substituted with 1 or 2 $R_{212}$ as defined above, (10)
    (i) benzo[b][thien-2-yl, (12a)
    (j) indol-2-yl, (12b)
    (k) benzo[b]thiazol-2-yl, (12c)
    (l) benzimidazol-2-yl, (12d)
    (m) 4-[2-[4-[2,6-bis(1-pyrrolidinyl)-4-pyrimidinyl]-1-piperazinyl]ethyl]-piperazinyl, (13)
    (n) 1,2,4-triazin-3-yl optionally substituted at the 5- and/or 6- position with $R_{212}$ as is defined above, (14)
  (2) (1-piperazinyl)(-$C_2-C_4$)alkyl optionally substituted in the 4- position with $-X_1$ or $-X_2$ as defined above,
  (3) $-X_2$, as defined above,
  (4) $-(CH_2)_m-X_4$ where m is as defined above and where $X_4$ is
    (a) $-O-CH_2CH_2-Y$, where Y is $C_1-C_3$ alkylamino, di($C_1-C_3$)alkylamino where the alkyl groups are the same or different, $C_3$-$C_6$ alkyleneimino, optionally substituted with 1 or 2 $C_1$-$C_3$ alkyl, (b) —$NR_{220}CH_2CH_2$—Y, where $R_{220}$ is —H or $C_1$-$C_3$ alkyl and Y is as defined above, (c) —$(CH_2)_g$—$N(R_{220})$—$X_2$, where g is 2, 3 or 4, and where $R_{220}$ and $X_2$ are as defined above, [H]

(5) —$(CH_2)_m$—$NR_{222}R_{223}$, where $R_{222}$ is —H or $C_1$-$C_3$ alkyl and $R_{223}$ is —$X_1$ or —$X_2$ as defined above, or $R_{222}$ and $R_{223}$ are taken together with the attached nitrogen atom to form a saturated mono-nitrogen $C_3$-$C_6$ heterocyclic ring and where m is as defined above, [I]

(6) —$(CHCH_3)_b$—$(CH_2)_f$—$R_{224}$, where b is 0 and f is 1 through 3 or b is one and f is 0 through 3, where $R_{224}$ is phenyl substituted with 1 through 3 —OH, $C_1$-$C_3$ alkoxy, —$NR_{225}R_{226}$ where $R_{225}$ and $R_{226}$ are the same or different and are —H, $C_1$-$C_3$ alkyl or are taken together with the attached nitrogen atom to form a $C_4$-$C_7$ cyclicamino ring, [J]

(7) —$(CH_2)_i$—$X_2$, where i is 1 through 4 and $X_2$ is as defined above, [K]

(8) (1-piperazinyl)acetyl substituted in the 4-position by $X_2$ where $X_2$ is as defined above, [L]

(9) (1-piperazinyl)carbonylmethyl substituted in the 4- position by —$X_2$ where $X_2$ is as defined above, and [M]

(B) $R_{210}$ is (1) —H, (2) $C_1$-$C_3$ alkyl, (3) $C_5$-$C_7$ cycloalkyl, (4) —$(CH_2)_m$—$NR_{211}$—$X_2$, where m, $R_{211}$ and $X_2$ are as defined above, [A]

(5) (1-piperazinyl)-$(C_2$-$C_4)$alkyl optionally substituted in the 4-position with —$X_1$ or —$X_2$ as defined above, [B]

(6) —$(CH_2)_m$—$X_4$, where m and $X_4$ are as defined above, [H]

(7) —$(CH_2)_m$—$NR_{222}R_{223}$, where m, $R_{222}$ and $R_{223}$ are as defined above, [I]

(8) —$(CHCH_3)_b$—$(CH_2)_f$—$R_{224}$, where b, f and $R_{224}$ are as defined above, [J]

(C) $R_{21}$ and $R_{210}$ are taken together with the attached nitrogen atom to form a heterocyclic ring selected from the group consisting of (1) 2-(carboxy)-1-pyrrolidinyl optionally as the $C_1$-$C_3$ alkyl ester or as a pharmaceutically acceptable salt, [C-1]

(2) 2-(carboxy)-1-piperidinyl optionally as the $C_1$-$C_3$ alkyl ester or as a pharmaceutically acceptable salt [C-2]

(3) 2-(carboxy)-1-hexamethyleneimino optionally as the $C_1$-$C_3$ alkyl ester or as a pharmaceutically acceptable salt, [C-3]

(4) 2-(carboxy)-1-heptamethyleneimino optionally as the $C_1$-$C_3$ alkyl ester or as a pharmaceutically acceptable salt, [C-4]

(5) 1-piperazinyl substituted in the 4-position with $R_{228}$—CO—$(CH_2)_j$— where $R_{228}$ is —$X_1$, —$NR_{229}X_1$ and 2-furanyl, where $R_{229}$ is —H or $C_1$-$C_3$ alkyl, where j is 0 through 3 and $X_1$ is as defined above, [D]

(6) 1-piperazinyl substituted in the 4-position with $X_2$—$(CH_2)_j$—, where $X_2$ and j are as defined above, [E]

(7) 1-piperazinyl substituted in the 4-position with $X_1$—$(CH_2)_j$—, where $X_1$ and j are as defined above, [F]

(8) 4-hydroxy-1-piperidinyl substituted in the 4-position with $X_1$ as defined above, [G]

(9) 1-piperazinyl substituted in the 4-position with $X_2$—$NR_{229}$—CO—$(CH_2)_i$—, where $X_2$, $R_{229}$ and i are as defined above; [N]

(D-II) $R_{16}$ is $\alpha$-$R_{163}$:$\beta$-$R_{164}$ where one of $R_{163}$ and $R_{164}$ is —H and the other is —H, —F, —$CH_3$ or —OH, and $R_{17}$ is —CH—$(CH_2)_p$—$NR_{21}R_{210}$, where p is 1 or 2, where $R_{21}$ and $R_{210}$ are as defined above.

(D-III) $R_{16}$ is $\alpha$-$R_{165}$:$\beta$-$R_{166}$ and $R_{17}$ is $\alpha$-$R_{175}$:$\beta$-$R_{176}$, where $R_{165}$ is —H, —OH, —F or —$CH_3$ and $R_{166}$ is —H, —OH, —F, or —$CH_3$, with the proviso that at least one of $R_{165}$ and $R_{166}$ is —H, where $R_{175}$ is —H, —OH, —$CH_3$, —$CH_2CH_3$, $C_2$-$C_7$ alkanoyloxy or —O—CO—$X_1$, where $X_1$ is as defined above, and where $R_{176}$ is —C(=Z)—$(CH_2)_n$—$NR_{21}R_{210}$, where Z, n, $R_{21}$ and $R_{210}$ are as defined above;

(D—IV) the 16,17—acetonide of a compound where $R_{165}$ is —OH, $R_{166}$ is —H, $R_{175}$ is —OH and $R_{176}$ is —C(=Z)—$(CH_2)_n$—$NR_{21}R_{210}$, where Z, n, —$R_{21}$ and $R_{210}$ are as defined above;

and pharmaceutically acceptable salts thereof, and hydrates and solvates thereof;

with the following overall provisos that:

(I) one of $R_{161}$ or $R_{162}$ is taken together with one of $R_{171}$ or $R_{172}$ to form a second bond between $C_{16}$ and $C_{17}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$:$\beta$-$R_{1010}$, (II) $R_{17}$ is —CH—$(CH_2)_p$—$NR_{21}R_{210}$, only when $R_{10}$ is $\alpha$-$R_{101}$:$\beta$-$R_{102}$, a-$R_{103}$:$\beta$-$R_{104}$, $\alpha$-$R_{107}$:$\beta$-$R_{108}$ or $\alpha$-$R_{109}$:$\beta$-$R_{1010}$, (III) $R_5$ and $R_{10}$ taken together are =CH—CH=C(OR_3)—CH=, only when $R_{17}$ is $\alpha$-$R_{175}$:$\beta$-$R_{176}$ or the 16,17-acetonide of a compound where $R_{16}$ is $\alpha$-OH:$\beta$-H and $R_{17}$ is $\alpha$-OH:$\beta$-C(=Z)—$(CH_2)_n$—$NR_{21}R_{210}$, and (IV) $R_5$ is $\alpha$-$R_{57}$:$\beta$-$R_{58}$, only when $R_{17}$ is $\alpha$-$R_{175}$:$\beta$-$R_{176}$ or $\alpha$-OH:$\beta$-C—(=Z)—$(CH_2)_n$—$NR_{21}R_{210}$, or the 16,17-acetonide thereof.

2. The method according to claim 1 wherein a formulation containing between 0.01 and 5% by weight of the agent is administered by subconjunctival injection.

3. The method according to claim 2 wherein a formulation containing between 0.05 and 2% by weight of the agent is administered.

4. The method according to claim 2 wherein the agent is administered in a polymeric carrier.

5. The method according to claim 4 wherein the agent is administered in a dextran or polysorbate 80 vehicle.

6. The method according to claim 5 wherein the agent is administered in a formulation containing disodium edetate, sodium sulfite, and or sodium chloride.

7. The method according to claim 4 wherein the agent is administered in a formulation containing sodium hydroxide or hydrogen chloride for adjustment of pH.

8. The method according to claim 1 wherein a formulation containing between 0.001 and 1% by weight of the agent is administered by intracameral or intravitreal injection.

9. The method according to claim 8 wherein a formulation containing between 0.005 and 0.15% by weight of the agent is administered in solution.

10. The method according to claim 8 wherein the agent is administered in a vehicle containing phosphate buffered saline, citrate buffered saline, or chrondroitin sulfate, or in a polymeric carrier such as sodium hyaluronate, hyaluronic acid, purified polyacrylamide or polysorbate 80.

11. The method according to claim 10 wherein the agent is administered in a formulation containing sodium hydroxide or hydrogen chloride for adjustment of pH.

12. The method of claim 1 wherein the agent is selected from the $C_{20}$ through $C_{26}$ aminosteroids of formula XI and pharmaceutically acceptable salts, hydrates or solvates thereof which function as antioxidants.

13. The method of claim 12, wherein the agent is selected from the $C_{21}$ aminosteroids of the formula XI or pharmaceutically acceptable salts, hydrates or solvates thereof which inhibit lipid peroxidation.

14. The method of claim 1 wherein the agent is selected from the $C_{21}$ aminosteroids of formula XI and pharmaceutically acceptable salts, hydrates, or solvates thereof.

15. The method of claim 1 wherein the agent is selected from U-74006 or pharmaceutically acceptable salts, hydrates or solvates thereof.

16. The method of claim 1 wherein the agent is selected from U-74500 or pharmaceutically acceptable salts, hydrates or solvates thereof.

17. The method of claim 1 wherein the agent is selected from U-75412 or pharmaceutically acceptable salts, hydrates or solvates thereof.

* * * * *